United States Patent [19]

Petrov et al.

[11] Patent Number: 5,241,079
[45] Date of Patent: Aug. 31, 1993

[54] PROCESS FOR PREPARING PERFLUORO-OXYAZIRIDINES

[75] Inventors: Viatcheslav A. Petrov; Darryl D. Desmarteau, both of Clemson, S.C.; Letanzio Bragante, Padova, Italy

[73] Assignee: Ausimont, S.p.A., Milan, Italy

[21] Appl. No.: 824,328

[22] Filed: Jan. 23, 1992

[30] Foreign Application Priority Data

Jan. 25, 1991 [IT] Italy ............................ MI91A000188

[51] Int. Cl.$^5$ ........................................... C07D 269/00
[52] U.S. Cl. .................................................. 548/959
[58] Field of Search ........................................ 548/959

[56] References Cited

U.S. PATENT DOCUMENTS

| | | | |
|---|---|---|---|
| 4,178,292 | 12/1979 | Tellier et al. | 548/959 |
| 4,287,128 | 9/1981 | Ratcliffe | 260/348.23 |
| 4,874,875 | 10/1989 | Navarrini et al. | 548/959 |

FOREIGN PATENT DOCUMENTS 0338585 10/1989 European Pat. Off. .
0743940 1/1956 United Kingdom .

OTHER PUBLICATIONS

L. Bragante et al., Journal of Fluorine Chemistry 53, 181–197 (1991).
R. G. Pews, Journal of Organic Chemistry, 32, 1628 (1967).
Zheng and DesMarteau, J. Org. Chem. 48, 4844 (1983).
DesMarteau, Inorg. Chem. 9, 2179 (1970).
Bernstein, Hohorst and DesMarteau, J. Am. Chem. Soc. 93, 3882 (1971).
Inorg. Chem. 14, 1223 (1975) by K. E. Peterman and J. M. Shreeve.
Falardeau et al., "Direct Synthesis of Fluorinated Peroxides", *J. Am. Chem. Soc.*, 98:12, pp. 3529–3532, (1976).

*Primary Examiner*—Joseph Paul Brust
*Assistant Examiner*—Jacqueline Haley
*Attorney, Agent, or Firm*—Bryan Cave

[57] ABSTRACT

A process for preparing perfluoro-oxyaziridines of formula:

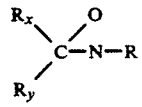

where $R_x$ and $R_y$, like or different from each other, are F or a $C_1$–$C_{10}$ perfluoroalkyl group, $R_z$ is a $C_1$–$C_{10}$-perfluoroalkyl group. The process consists in reacting the corresponding perfluoroimine with a perfluoroalkyl fluoroformyl peroxide $R_fOOC(O)F$, in the presence of an alkali metal fluoride MF, at a temperature ranging from $-40°$ to $+50°$ C.

3 Claims, No Drawings

PROCESS FOR PREPARING PERFLUORO-OXYAZIRIDINES

The present invention relates to a process for preparing perfluoro-oxyaziridines.

The simplest perfluoro-oxyaziridine is perfluoro-2-azapropene oxide:

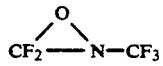

A process for preparing this compound has been described by Falardeau and DesMarteau in J.Am.-Chem.Soc., 98, 3529 (1976). It comprises the addition of trifluoromethyl hydroperoxide $CF_3OOH$ to the corresponding imine $CF_3N=CF_2$ and the subsequent conversion of the resulting hydroperoxide to oxyaziridine through NaF.

The same two-step process has been utilized by Zheng and DesMarteau (J.Org.Chem., 48, 4844 (1983)) for preparing oxyaziridines of formula:

from the corresponding imines.

This process exhibits several drawbacks. Apart from the fact that two distinct passages are required, by means of such process it is not possible to prepare oxyaziridines substituted, on the carbon atom, by perfluoroalkyl groups.

The hydroperoxide $CF_3OOH$ is preparable through a two-step process, as is illustrated by the following reaction scheme:

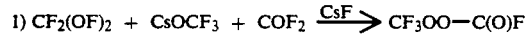

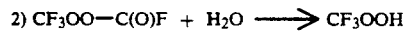

Reaction 1) is described by DesMarteau in Inorg.-Chem., 9, 2179 (1970), reaction 2) by Bernstein, Hohorst and DesMarteau in J.Am.Chem.Soc., 93, 3882 (1971).

The Applicant has now surprisingly found that it is possible to prepare perfluoro-oxyaziridines through a single-step process, by reacting the corresponding perfluoroimines with a perfluoroalkyl-fluoroformyl peroxide of general formula $R_fOOC(O)F$, in the presence of an alkali metal fluoride MF.

Said reaction can be conducted on both substituted and non-substituted perfluoroimines.

Thus, an object of the present invention is a process for preparing perfluoro-oxyaziridines of formula:

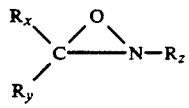

wherein:
$R_x$ and $R_y$, like or different from each other, are F or a perfluoroalkyl group having 1 to 10 carbon atoms, $R_z$ is a perfluoroalkyl group having 1 to 10 carbon atoms. The process consists in reacting a perfluoroimine of formula:

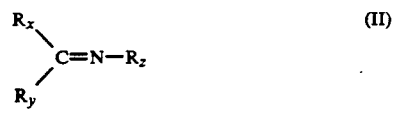

where $R_x$, $R_y$ and $R_z$ are the same as defined hereinabove, with a perfluoroalkyl-fluoroformyl peroxide $R_fOOC(O)F$, $R_f$ being a perfluoroalkyl group having 1 to 4 carbon atoms, in the presence of an alkali metal fluoride MF, at a temperature ranging from $-40°$ to $+50°$ C.

The perfluoroalkyl groups represented by $R_x$, $R_y$ and $R_z$ have preferably 1 to 6 carbon atoms.

The starting perfluoroimines are known compounds and can be prepared according to the methods described, for example, in "Organic Fluorine Chemistry" by W. A. Sheppard and C. M. Sharts, W. A. Benjamin Inc. (1969) and in Inorg.Chem., 14, 1223 (1975) by K. E. Peterman and J. M. Shreeve.

A compound of formula $R_fOOC(O)F$, preparable according to the method described by DesMarteau in Inorg.Chem., 9, 2179 (1970) is utilized as an oxidant.

It is to be pointed out that such method corresponds to reaction 1) of the above-illustrated scheme for preparing $CF_3OOH$. In other words, the oxidant utilized in the present invention is an intermediate for preparing the peroxide utilized in the Falardeau and DesMarteau process.

As already said, $R_f$ is a perfluoroalkyl group having 1 to 4 carbon atoms, preferably it is $—CF_3$.

The fluoride MF is, for example, a Na, K, Cs or Rb fluoride. CsF is preferably used.

Before being used, fluoride MF is usually dried by means of conventional techniques, for example by heating in an oven at temperatures higher than 100° C.

The reaction temperature ranges from $-40°$ to $+50°$ C., preferably from $-15°$ to $+30°$ C.

The peroxide/imine molar ratio generally ranges from 1:1 to 2:1, preferably from 1:1 to 1.3:1.

The fluoride MF/peroxide molar ratio generally ranges from 0.1:1 to 50:1, preferably from 5:1 to 10:1.

The reaction time is not a critical parameter and it is a function of the selected reaction temperature. Generally, the reaction is concluded in a time ranging from 30 minutes to 30 hours.

The perfluoro-oxyaziridines preparable by the process of the present invention are utilized for the synthesis of polymers or copolymers characterized by a high chemical inertia and a high thermal stability, such as the perfluoroaminoether polymers described in patent application EP-338,585.

The perfluoro-oxyaziridines can be also utilized in the preparation of nitrons. Furthermore, they form complexes with the ions of the transition metals, which act as catalysts for the photopolymerization of ethylene monomers.

The following examples are given for illustrative purposes and are by no way to be considered as a limitation of the scope of the present invention.

EXAMPLE 1

Into a Pyrex® 50 ml flask equipped with connections for a vacuum line and with a magnetic stirrer, there were introduced 2 g (13.2 mmols) of CsF. The fluoride had been previously dried in oven for two hours at 300°–400° C. The flask was then evacuated.

In the flask maintained at −196° C. there were condensed, through a Pyre vacuum line, 0.67 g (2.0 mmols) of $C_3F_7N=CFC_2F_5$ and 0.33 g (2.2 mmols) of $CF_2OOC(O)F$.

The reaction mixture was heated up to 22° C. in 10 minutes and was maintained under stirring at such temperature for 19 hours.

On conclusion of the reaction there were recovered, through distillation, 0.59 g (1.7 mmols) of the oxyaziridine of formula:

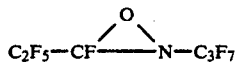

Yield: 85%.

The compound was characterized by the IR, $^{19}F$-NMR and mass spectra. The boiling point, determined according to the Sivoloboff method, was 73°–75° C.

EXAMPLE 2

1.3 g (3.0 mmols) of $C_4F_9N=CFC_3F_7$ were reacted with 0.52 g (3.5 mmols) of $CF_3OOC(O)F$ in the presence of 2.0 g (13.2 mmols) of CsF, following the procedure described in example 1.

After a 18-hour stirring at 22° C., there were recovered, through distillation, 1.1 g (2.45 mmols) of the oxyaziridine of formula:

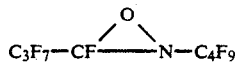

(yield: 82%).

The compound was characterized through the IR, $^{19}F$-NMR and mass spectra. The boiling point, determined according to the Sivoloboff method, was 118°–120° C.

EXAMPLE 3

0.57 g (2.0 mmols) of $(CF_2)_2CFN=CFCF_3$ were reacted with 0.33 g (2.2 mmols) of $CF_3OOC(O)F$ in the presence of 6.0 g (39.5 mmols) of CsF, following the procedure described in example 1.

After a 20 hour stirring at 22° C. there was recovered, by means of distillation, a 1:1 mixture of the starting imine and of the oxyaziridine of formula:

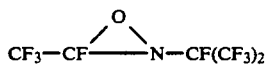

Through preparative gas-liquid chromatography (GLC) (column filling: 20% of Halocarbon K-352 on Chromosorb PAW), 0.18 9 (0.6 mmols) of pure oxyaziridine were isolated (yield: 30%).

The compound was characterized through the IR, $^{19}F$-NMR and mass spectra. The boiling point, determined through the Sivoloboff method, was 45°–46° C.

EXAMPLE 4

0.47 g (2.0 mmols) of $(CF_3)_2C=NCF_3$ were reacted with 0.33 g (2.2 mmols) of $CF_3OOC(O)F$ in the presence of 2.0 g (13.2 mmols) of CsF, following the procedure described in example 1.

After a 19 hour stirring at 22° C., there were recovered, through distillation, 0.27 g (1.1 mmols) of the oxyaziridine of formula:

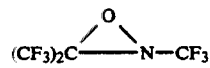

The compound was characterized through the IR, $^{19}F$-NMR and mass spectra.

COMPARATIVE EXAMPLE

A Pyrex® 100 ml flask equipped with a magnetic stirrer and connections for the vacuum, was cooled to −196° C. and then evacuated. In it there were condensed, through a Pyrex® vacuum line, 0.47 g (2.0 mmols) of $(CF_3)_2C=NCF_3$ and 0.20 g (2.0 mmols) of $CF_3OOH$.

The reactor was heated to 22° C. and maintained under stirring at such temperature for 19 hours.

Through distillation, 92% of the unreacted starting imine was obtained, while the hydroperoxide decomposed into $O_2$, $CO_2$, $CF_2O$ and $SiF_4$.

This comparative example proves that the process described by Falardeau and DesMarteau cannot be utilized for substituted imines.

We claim:

1. A process for preparing perfluorooxyaziridines of formula:

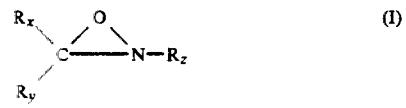

wherein:

$R_x$ is a perfluoroalkyl group having 1 to 10 carbon atoms, $R_y$ is F or a perfluoroalkyl group having 1 to 10 carbon atoms, and $R_z$ is a perfluoroalkyl group having 1 to 10 carbon atoms, comprising reacting a perfluoro-imine of formula:

wherein $R_x$, $R_y$ and $R_z$ are the same as defined hereinbefore, with a perfluoroalkyl-fluoroformyl peroxide $R_fOOC(O)F$, $R_f$ being a perfluoroalkyl group having 1 to 4 carbon atoms, in the presence of an alkali metal fluoride at a temperature ranging from −40° to +50° C.

2. The process of claim 1, wherien the perfluoroalkyl-fluoroformyl peroxide is $CF_3OOC(O)F$.

3. The process of claim 1, wherien the alkali metal fluoride is CsF.

* * * * *